United States Patent [19]

Decker et al.

[11] Patent Number: 5,623,082
[45] Date of Patent: Apr. 22, 1997

[54] PREPARATION OF ACYL CHLORIDES

[75] Inventors: Martin Decker, Ludwigshafen; Wolfgang Franzischka, Frankenthal; Rudolf Irnich, deceased, late of Bobenheim, by Erika Irnich, heiress; Manfred Sauerwald, Meckenheim, all of Germany

[73] Assignee: BASF Aktiengesellschaft, Ludwigshafen, Germany

[21] Appl. No.: 488,923

[22] Filed: Jul. 11, 1995

Related U.S. Application Data

[63] Continuation of Ser. No. 725,916, Jul. 3, 1991, abandoned, which is a continuation of Ser. No. 339,153, Apr. 17, 1989, abandoned.

[30] Foreign Application Priority Data

May 3, 1988 [DE] Germany ............ 38 14 969.9

[51] Int. Cl.⁶ .................................................. C07C 51/58
[52] U.S. Cl. ........................................ 554/231; 562/861
[58] Field of Search ........................ 554/231; 562/861

[56] References Cited

U.S. PATENT DOCUMENTS

| | | | |
|---|---|---|---|
| 3,318,950 | 5/1967 | Christoph, Jr. et al. | 562/857 |
| 4,880,576 | 11/1989 | Blank et al. | 562/828 |

FOREIGN PATENT DOCUMENTS

| | | |
|---|---|---|
| 620385 | 1/1963 | Belgium . |
| 0050779 | 5/1982 | European Pat. Off. . |
| 31504 | 12/1982 | European Pat. Off. . |
| 2057956 | 6/1972 | Germany . |
| 2085429 | 4/1982 | United Kingdom . |

*Primary Examiner*—Joseph Conrad
*Attorney, Agent, or Firm*—John H. Shurtleff

[57] ABSTRACT

Acyl chlorides are prepared by reacting a carboxylic acid or its anhydride with carbonyl chloride in the presence of a carboxamide of the formula I

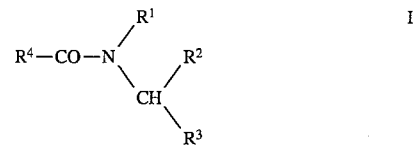

where $R^1$ is a radical of the formula

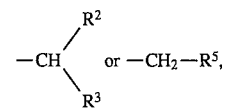

$R^2$ and $R^3$ are each alkyl of 1 to 9 carbon atoms, $R^4$ and $R^5$ are each hydrogen or alkyl of 1 to 9 carbon atoms and the two radicals $R^1$ and $R^2$ may furthermore be a hydrocarbon radical which completes the moiety

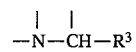

to form a heterocyclic structure, and the stated alkyl and hydrocarbon radicals may furthermore contain substituents which are inert under the reaction conditions.

9 Claims, No Drawings

PREPARATION OF ACYL CHLORIDES

This application is a continuation of Ser. No. 07/725,916, filed Jul. 3, 1991, now abandoned, which is a continuation, of application Ser. No. 339,153 filed Apr. 17, 1989 now abandoned.

The present invention relates to a process for the preparation of acyl chlorides by reacting a carboxylic acid or its anhydride with carbonyl chloride in the presence of a carboxamide.

Belgian Patent 620,385 and German Laid-Open Application DOS 2,057,956 disclose that carboxylic acids can be converted into the corresponding acyl chlorides with carbonyl chloride if the reaction is carried out in the presence of a dialkylcarboxamide as a catalyst.

The industrial production of the acyl chlorides by this process gives rise to difficulties, which are described in detail in European Patent 31,504. This patent states that the difficulties mentioned are avoided and the acyl chlorides are obtained in an industrially satisfactory manner if the dialkylformamide catalyst used is diisobutylformamide.

We have found that, in the preparation of acyl chlorides by reacting a carboxylic acid or its anhydride with carbonyl chloride in the presence of a carboxamide, substantially better results are obtained if the carboxamide used is a compound of the formula I

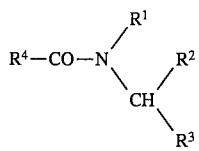

where $R^1$ is a radical of the formula

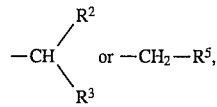

$R^2$ is alkyl of 2 to 9 carbon atoms $R^3$ is alkyl of 1 to 9 carbon atoms, $R^4$ and $R^5$ are each hydrogen or alkyl of 1 to 9 carbon atoms and the two radicals $R^1$ and $R^2$ may furthermore be a hydrocarbon radical which completes the moiety

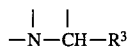

to form a heterocyclic structure, and the stated alkyl and hydrocarbon radicals may furthermore contain substituents which are inert under the reaction conditions.

The carboxamides to be used according to the invention, which, in contrast to the dialkylamides already used, carry a secondary carbon atom —CH< on the nitrogen atom, surprisingly permit the preparation of the acyl chlorides in high yield and purity. Another unexpected advantage of these catalysts is that they permit a higher throughput in a given production plant. They also have good activity even in very low concentration, so that the disadvantages due to the catalyst, such as precipitation of solids, deposition of resin or contamination of the crude product by strongly colored decomposition products of the catalyst, which are encountered when the conventional dialkylcarboxamides are used, occur to a greatly restricted extent, if at all. The catalysts to be used according to the invention have the further advantage that they still result in a high reaction rate even with less than the stoichiometric amount or a very small excess of carbonyl chloride, so that the process can be carried out with the consumption of less energy.

In the dialkylcarboxamides of the formula I to be used according to the invention, the alkyl radicals may be straight-chain or branched and are of 1 to 9 carbon atoms. Examples are methyl, ethyl, propyl, isopropyl, butyl, isobutyl, pentyl and hexyl. Both the alkyl radicals and the hydrocarbon radicals formed by $R^1$ and $R^2$ may contain substituents which are inert under the reaction conditions, for example halogen, such as chlorine or bromine, alkoxy, such as methoxy or ethoxy, and alkoxy-carbonyl, such as methoxycarbonyl or ethoxycarbonyl. The hydrocarbon radicals which form the heterocyclic structure may furthermore contain alkyl groups, such as methyl or ethyl. Examples of suitable heterocyclic structures are pyrrolidine, piperidine and hexamethyleneimine rings.

Preferred carboxamides are those of the formula I where the alkyl groups $R^2$, $R^3$ and $R^5$ are each of 1 to 4 carbon atoms. Of particular industrial interest is the use of dialkylcarboxamides of the formula

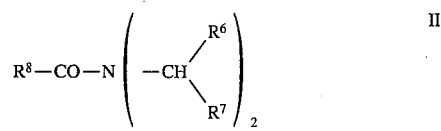

where $R^6$ is alkyl of 2 to 4 carbon atoms, $R^7$ is alkyl of 1 to 4 carbon atoms and $R^8$ is hydrogen or alkyl of 1 to 6 carbon atoms. Examples are the following dialkylcarboxamides: di-sec-butylform-amide, di-3-pentylformamide, 3-pentyl-isopropylformamide, 1-formyl-2,6-dimethylpiperidine, 1-formyl-2,5-dimethylpyrrolidine and 1-propionyl-2,6-dimethylpiperidine.

Preferred starting materials are aliphatic carboxylic acids or their anhydrides. For example, carboxylic acids of the general formula R-COOH, where R is alkyl of 1 to 18 carbon atoms, are used as starting materials. The alkyl radical may furthermore contain substituents which are inert under the reaction conditions, such as chlorine, alkoxy or alkoxycarbonyl of 1 to 4 carbon atoms. Examples of suitable starting materials are the following: acetic acid, mono-, di- and trichloroacetic acid, propionic acid, butyric acid, valeric acid, lauric acid, stearic acid, caproic acid, isovaleric acid, palmitic acid, 2-ethylhexanecarboxylic acid and methoxyacetic acid.

The aliphatic carboxylic acid is reacted with the stoichiometric amount or, advantageously, with an excess of carbonyl chloride, preferably in a ratio of from 1.1 to 1.5 moles of carbonyl chloride per mole of the starting acid. The carboxamide of the formula I is advantageously used in an amount of from 0.005 to 1, preferably from 0.02 to 0.3, mol %, based on the carboxylic acid. It is also possible to use larger amounts of carboxamide, for example up to 5 mol %. Advantageously, however, a very small amount of carboxamide is used, since this facilitates the further processing of the acyl chlorides obtained. The reaction is carried out at from 30° to 150° C., preferably from 50° to 100° C., under atmospheric or superatmospheric pressure and batchwise or continuously.

In the batchwise preparation of acyl chlorides, the reaction is carried out, for example, by a procedure in which the liquid or molten carboxylic acid is initially taken in a suitable stirred container, the carboxamide is dissolved therein and the mixture is heated to the desired reaction temperature. Introduction of carbonyl chloride can be started as early as during the heating up stage. As soon as the stoichiometric amount of carbonyl chloride has been metered in, the amount fed in per unit of time is decreased to 10–30% of the original amount. The end of the reaction is indicated by strong refluxing of the carbonyl chloride. The crude product is worked up by distillation, the first fraction of the acyl chloride containing the carbonyl chloride used in excess. This fraction is gradually reacted with the initially taken carboxylic acid in the subsequent batch as soon as the carbonyl chloride feed is begun.

In the continuous procedure, the reactor is first filled with carboxylic acid and catalyst to a level close to the overflow. Thereafter, the carboxylic acid is reacted with carbonyl chloride at the desired reaction temperature. Carboxylic acid, carboxamide and carbonyl chloride are then fed to the reactor simultaneously and continuously. The hourly volume flow of the carboxylic acid, which is generally from 10 to 40% of the reaction. volume, can be increased to 50–80% of the reactor volume, particularly in the case of fairly high molecular weight carboxylic acids.

The carboxamide is added continuously. It can also be dissolved beforehand in the carboxylic acid and fed to the reactor together with this. In the continuous procedure, the amount of carbonyl chloride can be restricted to a few mol % above the stoichiometric amount, because the excess carbonyl chloride is separated off in a column downstream of the reactor and is immediately recycled to the reactor.

The compounds which can be prepared by the process of the invention are solvents or useful starting materials for the preparation of solvents, scents, plasticizers, detergents, peroxides, mordants and pesticides. Regarding their use, reference may be made to the stated publications and to Ullmanns Encyklopädie der technischen Chemie, Volume 5, page 100 et seq and 393 et seq.

EXAMPLE 1

144 parts by weight of 2-ethylhexanoic acid and 0.31 part by weight (0.2 mol %) of di-sec-butylformamide are initially taken in a stirred container equipped with an overflow, a reflux condenser and feed means and having a capacity of 300 parts by volume up to the overflow. By passing in carbonyl chloride at 70° C., the 2-ethylhexanoic acid is completely converted into the acyl chloride. The temperature of the coolant in the reflux condenser is −70° C. 184 parts by weight of 2-ethylhexanoic acid, in which 0.2 mol % of di-sec-butylformamide is dissolved, and 145 parts by weight of carbonyl chloride are now passed, per hour, into the reaction mixture at 70°.

The crude reaction product flows from the over-flow of the stirred reactor into a stock vessel, from which it is fed for further processing. The crude 2-ethylhexanoyl chloride is obtained in 99.9% purity and has an iodine color number of 80.

EXAMPLES 2 TO 4

The acids stated in the Table are converted into the acyl chlorides in a similar manner, under the conditions stated there. Where the excess carbonyl chloride condenses in the working up stage and is recycled to the reaction stage, the feed of fresh carbonyl chloride is reduced virtually to the stoichiometric amount.

In the working up stage, the reaction product is purified by distillation, if the volatility of the product permits this. In the case of sparingly volatile compounds, purification may be effected with active carbon. However, because of the good quality of the crude products, further purification can be dispensed with in many cases.

If, in Example 4, the amount of catalyst is halved stepwise to 0.1 mol % or 0.05 mol % or 0.025 mol %, the iodine color number of the crude tallow fatty acid chloride is reduced stepwise to 30. The reaction temperatures in this procedure are 70° C. or 80° C. or 100° C.

EXAMPLE 5 (COMPARATIVE EXAMPLE)

In the apparatus described in Example 1 and in a similar manner, 144 parts by weight of 2-ethylhexanoic acid and 0.311 part by weight (0.2 mol %) of diisobutyl-formamide are completely converted into the acyl chloride with carbonyl chloride at 70° C. 81.5 parts by weight of 2-ethylhexanoic acid, in which 0.2 mol % of diisobutyl-formamide is dissolved, and 65 parts by weight of carbonyl chloride are now passed, per hour, into the reaction mixture at 70° C. The crude product obtained contains 99.2% of 2-ethylhexanoyl chloride and 0.2% of 2-ethyl-hexanoic anhydride. It has an iodine color number of 150.

EXAMPLES 6 TO 8 (COMPARATIVE EXAMPLES)

The acids stated in the Table are converted into the acyl chlorides in a similar manner, under the conditions stated there.

TABLE

| | | FEED | | | Purity of the actyl chloride | | |
| --- | --- | --- | --- | --- | --- | --- | --- |
| EXAMPLE | CARBOXYLIC ACID | ACID [PARTS BY WEIGHT/h] | COCL$_2$ | REACTION TEMPERATURE [°C.] | ACYL CHLORIDE [% BY WEIGHT] | ACID OR ANHYDRIDE [% BY WEIGHT] | IODINE COLOR NUMBER |
| 2 | Propionic acid | 83 | 120 | 60 | 99.0 | — | 60 |
| 3 | Isobutyric acid | 121 | 150 | 65 | 99.4 | — | 70 |
| 4 | Tallow fatty acid | 117 | 48 | 70 | 99.8 | — | 60 |
| 6 | Propionic acid | 74 | 110 | 58 | 96.9 | 2.9 | 120 |
| 7 | Isobutyric acid | 88 | 110 | 55 | 93.8 | 5.5 | 80 |
| 8 | Tallow fatty acid | 94 | 38 | 65 | 99.4 | — | 130 |

EXAMPLE 9

In a stirred reactor having a capacity of 500 parts by volume, 273 parts by weight of tallow fatty acid and 0.19 part by weight (0.1 mol %) of di-3-pentylform-amide are initially taken similarly to Example 9 and then reacted with carbonyl chloride at 90° C. The mixture is worked up similarly to Example 9, and 292 parts by weight: of crude tallow fatty acid chloride having an iodine color number of 20 are obtained. The acyl chloride has a purity of 99.8%. The yield is 99.5 mol %.

EXAMPLE 10

In the apparatus described in Example 1, 144 parts by weight of 2-ethylhexanoic acid are completely converted into the acyl chloride with carbonyl chloride at 80° C. in the presence of 0.185 part by weight (0.1 mol % of di-3-pentylformamide. 271 parts by weight of 2-ethylhexanoic acid, in which 0.348 part by weight of di-3-pentylformamide is dissolved, and 205 parts by weight of carbonyl chloride are passed, per hour, into the reaction mixture at 80° C. The crude 2-ethylhexanoyl chloride thus obtained has a purity of 99.8 % and an iodine color number of 40. A product as pale as water is obtained in virtually quantitative yield by distillation.

We claim:

1. A process for the preparation of an acyl chloride which comprises:

reacting a carboxylic acid or its anhydride with carbonyl chloride in the presence of a carboxamide selected from the group consisting of di-sec-butylformamide and di-3-pentylformamide.

2. A process as claimed in claim 1, wherein the reaction is carried out at from 30° to 150° C.

3. A process as claimed in claim 1, wherein said carboxamide I is di-sec-butylformamide.

4. A process as claimed in claim 1, wherein said carboxamide I is di-3-pentylformamide.

5. A process as claimed in claim 1, wherein not less than the stoichiometric amount of carbonyl chloride is used, based on the carboxylic acid or its anhydride.

6. A process as claimed in claim 1, wherein said carboxamide is used in an amount of from 0.005 to 1 mol % based on the carboxylic acid or its anhydride.

7. A process as claimed in claim 1, wherein said carboxamide is used in an amount of from 0.02 to 0.3 mol %, based on the carboxylic acid or its anhydride.

8. A process as claimed in claim 1, wherein said carbonyl chloride is used in a ratio of 1.1 to 1.5 moles per mole of said carboxylic acid or its anhydride.

9. A process for the preparation of an acyl chloride which comprises:

reacting a carboxylic acid or its anhydride with carbonyl chloride in the presence of a carboxamide of the formula

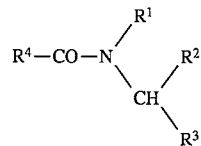

$R^1$ being a radical of the formula

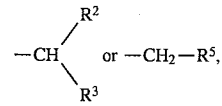

wherein:

$R^2$ is alkyl of 2 to 4 carbon atoms and $R^3$ is alkyl of 1 to 4 carbon atoms, with the proviso that the total of carbon atoms in $R^2$ and $R^3$ is not more than 7; $R^4$ is hydrogen or alkyl of 1 to 9 carbon atoms, $R^5$ is hydrogen or alkyl of 1 to 4 carbon atoms; and the two radicals $R^1$ and $R^2$ may furthermore be a hydrocarbon radical which completes the moiety

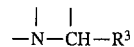

to form a heterocyclic structure having a total of not more than 7 carbon atoms, and wherein the stated alkyl and hydrocarbon radicals may furthermore contain substituents which are inert under the reaction conditions.

* * * * *